United States Patent
Detje et al.

(10) Patent No.: US 8,715,546 B2
(45) Date of Patent: May 6, 2014

(54) METHOD AND MATERIAL KIT FOR THE PRODUCTION OF TOOTH REPLACEMENT PARTS

(75) Inventors: Bernd Detje, Hamburg (DE); Hans-Dieter Höhnk, Reinbek (DE); Wolfgang Carl Friedrich Mühlbauer, Hamburg (DE)

(73) Assignee: Ernst Muehlbauer GmbH & Co. KG, Norderfriedrichskoog (DE)

( * ) Notice: Subject to any disclaimer, the term of this patent is extended or adjusted under 35 U.S.C. 154(b) by 1012 days.

(21) Appl. No.: 11/988,478

(22) PCT Filed: Jun. 14, 2006

(86) PCT No.: PCT/EP2006/005736
§ 371 (c)(1), (2), (4) Date: Jun. 15, 2009

(87) PCT Pub. No.: WO2007/006386
PCT Pub. Date: Jan. 18, 2007

(65) Prior Publication Data
US 2009/0311649 A1    Dec. 17, 2009

(30) Foreign Application Priority Data

Jul. 8, 2005 (DE) .................. 10 2005 032 044

(51) Int. Cl.
*A61C 13/00* (2006.01)

(52) U.S. Cl.
USPC .............................. 264/16; 264/19; 264/222

(58) Field of Classification Search
USPC .............................. 264/16, 19, 219, 222, 227
See application file for complete search history.

(56) References Cited

U.S. PATENT DOCUMENTS 5,911,580 A    6/1999    Sharp et al.
5,971,760 A    10/1999    Letcher et al.

FOREIGN PATENT DOCUMENTS

DE    26 46 364 A1    4/1978
WO    WO 98/35630 A    8/1998

*Primary Examiner* — Galen Hauth
(74) *Attorney, Agent, or Firm* — Alix, Yale & Ristas, LLP

(57) ABSTRACT

The process for producing tooth replacement parts is characterized in that curable tooth replacement material is introduced into a first mold of part of the human dentition, a positive model produced from a second mold is pressed into this material and the tooth replacement material remaining after the pressing-in is allowed to cure to form the tooth replacement part(s).

7 Claims, No Drawings

METHOD AND MATERIAL KIT FOR THE PRODUCTION OF TOOTH REPLACEMENT PARTS

BACKGROUND

The invention relates to a process and a materials kit for producing tooth replacement parts.

Various processes for producing firmly seated tooth replacements for artificial replacement or restoration of lost or greatly damaged teeth and for cosmetic-esthetic corrections are known. An aspect common to all of these is that they have to be produced in complicated processes by specially trained persons, which generally takes a number of days and the finished tooth replacement can only then be installed in the oral system of the patient.

Furthermore, the majority of these processes require a model of the upper and lower jaws which have to be installed precisely in a mechanical motion simulator (articulator) to reproduce important contact relationships between the tooth replacement and the remaining dentition. The model is also required to be able to achieve precise realization of the transition between the prepared tooth and a crown, bridge, inlay or veneer.

To create these models, the dentist prepares the teeth to be treated and then produces a mold of both jaws (negative) which is then converted into a working model (positive) by other persons (dental technicians) by filling with plaster or plastic. Modeling materials composed of specific silicone compounds are also known, e.g. as described in U.S. Pat. No. 5,911,580. Processes in which the plaster or plastic model is replaced by digital models which are created by measurement of the oral situation by means of laser or scanner light are also known.

SUMMARY

A process for producing tooth replacement parts makes the production of tooth replacement parts significantly simpler. This is said to make the work of a dental technician considerably easier.

Curable tooth replacement material is introduced into a first mold of part of the human dentition, pressing a positive model produced from a second mold into this material and allowing the tooth replacement material remaining after the pressing-in to cure to form the tooth replacement part(s).

The dental technician thus only needs to use the two molds produced by the dentist in order to produce the tooth replacement parts without further significant shaping.

DETAILED DESCRIPTION

As first mold, use is made of the mold of a human dentition in which missing tooth substance has been replaced. The dentist can thus provisionally supplement the dentition as it is to be after the treatment. He then takes the first mold from this. These provisional parts are subsequently removed and the dentition or the parts of the dentition are prepared in the customary way for accommodating the tooth replacement parts. The second mold is then taken from this.

These two molds are handed over to the dental technician who can then produce the tooth replacement parts in a simple manner as described.

It is not necessary for this to be carried out by a dental technician. The dentist could also make this himself. In this case, the process makes it possible to produce the tooth replacement quickly and inexpensively and install it in the teeth at only one sitting.

The positive model is advantageously shaped, in particular by cutting or milling, before being pressed into the tooth replacement material. In this way, it is possible, for example, to expose the preparation boundary. This exposure of the preparation boundary is in the case of installation of a crown critical for precise configuration of the edge.

Furthermore, it is advantageous for the tooth replacement part to be shaped after curing, for example by grinding or milling. In this way, it is possible, for example, to remove flashing which remains after pressing-in of the positive model and subsequent curing.

A materials kit for carrying out the process is characterized in that it contains the following materials:
a) a material for provisional restoration of lost tooth substance,
b) a curable, flowable material for producing a positive model,
c) a curable, flowable material for producing the tooth replacement.

The material for the provisional restoration of lost tooth substance is advantageously curable and able to be shaped by means of rotating instruments after curing. The material can therefore simply be applied to the tooth for preliminary tooth reconstruction, brought to its approximate shape by modeling and brought to the final shape by means of rotating instruments after curing.

The material b) is advantageously a hard silicone which has a Shore A hardness of at least 55, preferably from 80 to 95, or a Shore D hardness of at least 35-45.

The material c), from which the tooth replacement is produced, should after curing be permanently resistant to influences of the oral environment and have only a small polymerization shrinkage.

The materials kit advantageously comprises a molding material for making a mold of the reconstructed part of the dentition in which the missing tooth substance has been replaced and of the part of the dentition prepared for installation of the tooth replacement.

Furthermore, it preferably comprises a release agent in order to aid removal of the positive model from the second mold.

Finally, the materials kit advantageously comprises adhesives for affixing the parts which provisionally replace the missing tooth substance.

The process and the materials kit thus not only make the work of the dental technician easier but also assist that of the dentist for whom the making of molds is made considerably easier. The dentist can even dispense with the services of his dental technician if he employs the process of the invention. The process offers the patient the advantage that he can in this case obtain the tooth replacement in one sitting.

Thus, in a first step of the process, the lost hard substance of the tooth is restored by means of a buildup material which is preferably a curing material which can be shaped by means of rotating instruments. This material is preferably a composite or a plastic.

The positive model is formed by means of a curable flowable material which is preferably a hard silicone and can be shaped by cutting. The silicone for the positive model should after curing have a Shore A hardness of at least 55, preferably from 80 to 95, while the Shore D hardness determined in accordance with ISO 868-1985 should be from 35 to 45 or even more.

The material for producing the tooth replacement has to be a curing flowable material whose properties allow it to permanently withstand the influences of the oral environment and which has only a low polymerization shrinkage. It is preferably a composite or a plastic which is colored to give it the color of the teeth. The material should be able to be upgraded by means of a subsequent heat treatment. As a composite, it should have a flexural strength of at least 120 MPa, preferably from 140 to 175 MPa or even more. The compressive strength should be at least 350 MPa, preferably from 400 to 700 MPa or even more. The shrinkage should be not more than 2.5% by volume, preferably from ≤2 to 0.1% by volume or even less. The material wear (abrasion) should be not more than 80 μm (200 000 cycles ACTA), preferably in the range from 50 to 1 μm.

As molding material for making the mold of the reconstructed dentition or part of the dentition and for making the mold of the prepared dentition or part of the dentition, preference is given to using a silicone. A release agent to enable the positive model to be taken from the mold is likewise advantageous. Finally, adhesives should be provided for installation of the buildup material on the hard substance of the tooth.

As mentioned, the process of the invention is advantageously carried out by a dental technician. However, it is also possible for the dentist himself to employ this process without the aid of a dental technician. In this case, the following sequence is employed.

In a first working step, the anatomical shape of the tooth is restored. Even lost approximal and/or occlusal contact points can be restored. Correction of tooth shape and/or tooth position is also possible. The process can also be used for closing gaps in the case of missing teeth. To restore the desired tooth shape, a light-curing or self-curing plastic or composite is preferably used. This can be applied and modeled by means of manual instruments or be manipulated by means of manual instruments after application. After curing has occurred, fine shaping by means of rotating instruments can be carried out so as to restore, for example, an exact occlusal contact relationship. The material can also be fixed adhesively to the hard substance of the tooth in order to serve as buildup filling for the preparation. Materials such as cements, gypsum plasters, waxes, thermoplastics or silicones are also conceivable for this purpose.

When the appropriate measures for provisional reconstruction of the tooth shape or shape of the dentition are complete, a first mold is made by means of customary molding techniques and molding materials. The tooth/teeth to be attended to is/are then prepared. This is effected according to the customary rules for the accommodation of tooth replacement parts.

When these preparation measures are complete, a mold of the now prepared teeth (second mold) is made by means of customary molding techniques using appropriate molding materials.

The second mold is filled with a flowable, curable material, preferably a silicone. After curing of the silicone, the positive model obtained is taken from the second mold. To avoid sticking of the material of the positive model to the molding material, it may be necessary to use a release agent. The positive model created in this way can, if necessary, be shaped further by cutting or milling, e.g. to expose the preparation boundary. Materials such as cements, gypsum plasters, plastics or thermoplastics are also conceivable for the production of this positive model.

The flowable, curable tooth replacement material is introduced into the first mold. The positive model is then placed on or inserted into the filled mold with positive contact. It is advisable to free the first mold of all interfering excesses before filling with the tooth replacement material. Curing of the tooth replacement material is subsequently awaited.

After the tooth replacement material has cured, the first mold is separated from the model and the shaped blank is taken from the first mold or taken off from the positive model. The shape and size of the blank corresponds to the reconstructed tooth situation. To improve the physical properties of the blank, it can be upgraded by subsequent heat treatment.

The blank is freed of any excesses of material and shaped by means of rotating instruments until a satisfactory edge contact is achieved on the positive model. It is also possible to undertake shape corrections. If desired, color corrections can be carried out by means of curing color pastes. The tooth replacement is subsequently polished and inserted into the mouth of the patient without fastening material. The fitting of the edge, the approximal contact points and the occlusal contact points are checked and if necessary corrected by grinding. After-polishing is carried out if necessary. It is also possible to widen the contact points by application of tooth replacement material. The finished tooth replacement is then affixed in the mouth by means of a suitable fastening material using customary methods and the occlusal contact points are checked again.

The advantages of the process are that the tooth replacement can also be produced in the dental practice without a dental technician being required and that it can be produced and used during one treatment sitting. The tooth replacement can be reproduced inexpensively and quickly and can be produced sufficiently precisely despite the low technical effort. This applies in particular to the edge configuration. Only few materials and only few instruments are necessary.

The invention claimed is:

1. A process for producing tooth replacement parts, in which curable tooth replacement material is introduced into a first mold taken of at least a part of the actual human dentition, a positive model produced from a second mold is pressed into this material and the tooth replacement material remaining after the pressing-in is allowed to cure to form the tooth replacement part(s), wherein the second mold is a mold taken of at least a part of an actual human dentition which has been prepared for installation of the tooth replacement part(s), characterized in that said at least a part of the actual human dentition is provisionally supplemented as it is to be after the treatment so that the anatomical shape of the teeth is restored, and said first mold is made of the actual human dentition as provisionally supplemented.

2. The process as claimed in claim 1, characterized in that the positive model is shaped before pressing into the tooth replacement material.

3. The process as claimed in claim 2, characterized in that the positive model is shaped by cutting or milling.

4. The process as claimed in claim 1, characterized in that the tooth replacement part is shaped after curing.

5. The process as claimed in claim 4, characterized in that the tooth replacement part is shaped by grinding or milling.

6. The process as claimed in claim 2, characterized in that the tooth replacement part is shaped after curing.

7. The process as claimed in claim 3, characterized in that the tooth replacement part is shaped after curing.

* * * * *